United States Patent [19]

Wätjen

[11] Patent Number: 4,772,599
[45] Date of Patent: Sep. 20, 1988

[54] BENZODIAZEPINE DERIVATIVES AND THEIR PREPARATION AND USE

[75] Inventor: Frank Wätjen, Vaerloese, Denmark

[73] Assignee: A/S Ferrosan, Søborg, Denmark

[21] Appl. No.: 25,614

[22] Filed: Mar. 13, 1987

[30] Foreign Application Priority Data

Apr. 16, 1986 [DK] Denmark .............................. 1740/86

[51] Int. Cl.$^4$ .................... A61K 31/55; C07D 487/14;
C07D 548/131; C07D 521/000
[52] U.S. Cl. .................................... 514/220; 548/498;
548/504; 548/506
[58] Field of Search ........................ 540/498; 514/220

[56] References Cited

U.S. PATENT DOCUMENTS

| | | | |
|---|---|---|---|
| 4,316,839 | 2/1982 | Gerecke et al. | 540/498 |
| 4,435,403 | 3/1984 | Braestrup et al. | 546/86 |
| 4,507,313 | 3/1985 | Braestrup et al. | 540/498 |

FOREIGN PATENT DOCUMENTS

| | | | |
|---|---|---|---|
| 245/85 | 1/1985 | Denmark | 540/498 |
| 27214 | 4/1981 | European Pat. Off. | 540/498 |
| 54507 | 6/1982 | European Pat. Off. | 546/86 |
| 109921 | 3/1984 | European Pat. Off. | 540/498 |
| 150040 | 7/1985 | European Pat. Off. | 540/498 |
| 3149/84 | 6/1984 | Switzerland | 540/498 |
| 5123/84 | 10/1984 | Switzerland | 540/498 |
| 225/84 | 1/1985 | Switzerland | 540/498 |

OTHER PUBLICATIONS

Squires, Braestrup, "Benzodiazepine Receptors in Rat Brain", Nature, 266, (1977), pp. 732-734.
Litchfield et al., "A Simplified Method of Evaluating Dose-Effect Experiments", Journal of Pharmacology and Experimental Therapeutics, (1949), pp. 99-113.
Hartman et al., "A Novel 1,3-thiazole Synthesis via alpha-metallated isocyanides and thiono esters", Synthesis, (1976), pp. 681-682.
Chang et al., "Benzodiazepine Receptors: Labeling in Intact Animals with [$^3$H] Flunitrazepam", Europe. J. Pharmacol., 48, (1978), pp. 213-218.

Primary Examiner—Robert T. Bond
Attorney, Agent, or Firm—Gordon W. Hueschen

[57] ABSTRACT

New benzodiazepine derivatives of the general formula

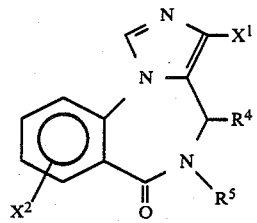

wherein
X$^1$ and X$^2$ independently are

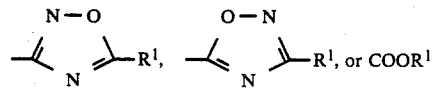

wherein
R$^1$ is C$_{1-3}$-alkyl, C$_{3-5}$-cycloalkyl, C$_{1-3}$-alkoxymethyl, C$_{1-3}$-hydroxyalkyl, or aryl,
R$^4$ is hydrogen, and
R$^5$ is C$_{1-6}$-alkyl, or wherein R$^4$ and R$^5$ together form a 2-4 membered alkylene chain.

The compounds are useful in psychopharmaceutical preparations as anticonvulsants, anxiolytics, hypnotics, and nootropics.

11 Claims, No Drawings

BENZODIAZEPINE DERIVATIVES AND THEIR PREPARATION AND USE

The present invention relates to therapeutically active benzodiazepine derivatives, a method of preparing the same, pharmaceutical compositions comprising the compounds, and to methods of treating therewith. The novel compounds are useful in psychopharmaceutical applications, e.g., in the treatment of central nervous system ailments, for example, as anticonvulsants or anxiolytics.

It is well known (Squires, R.F. and Braestrup, C. in Nature (London) 266 (1977) 732–734) that specific sites in the central nervous systems of vertebrates exhibit a high specific affinity for binding 1,4- and 1,5-benzodiazepines. These sites are called benzodiazepine receptors.

European patent applications Nos. 109,921 and 150,040 disclose oxadiazolyl derivatives of imidazobenzodiazepines.

The novel compounds of the invention are imidazobenzodiazepine derivatives having the general formula I

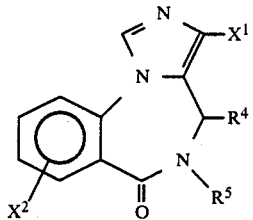

wherein
$X^1$ and $X^2$ independently are

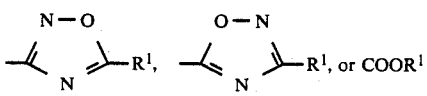

wherein
$R^1$ is $C_{1-3}$-alkyl, $C_{3-5}$-cycloalkyl, $C_{1-3}$-alkoxymethyl, $C_{1-3}$-hydroxyalkyl, or aryl,
$R^4$ is hydrogen, and
$R^5$ is $C_{1-6}$-alkyl, or wherein $R^4$ and $R^5$ together form a 2-4 membered alkylene chain.

The invention also relates to a method of preparing the above mentioned compounds. This method comprises:
(a) reacting a compound of formula II

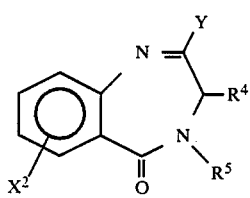

wherein $R^4$, $R^5$ and $X^2$ have the meanings set forth above and wherein Y is a leaving group, with a compound having the formula III

(III)

wherein $X^1$ has the meaning set forth above, to form a compound of the invention, or
(b) reacting a reactive derivative, such as an ester derivative, of a compound having the general formula IV

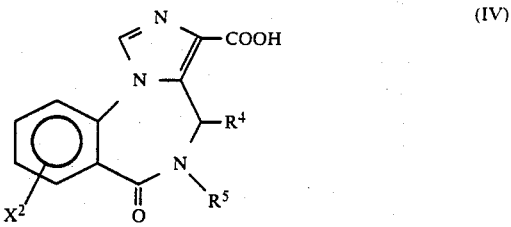

wherein $R^4$, $R^5$ and $X^2$ have the meanings set forth above, with a compound having the general formula V

(V)

wherein $R^1$ has the meaning set forth above to form a compound of the general formula I wherein $X^2$, $R^4$ and $R^5$ have the meanings defined above and wherein $X^1$ is

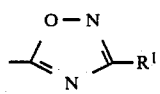

wherein $R^1$ has the meaning set forth above, optionally via an intermediate compound having the formula VI

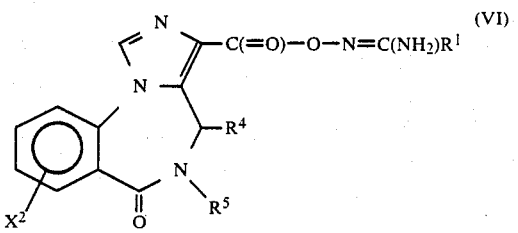

wherein $X^2$, $R^1$, $R^4$ and $R^5$ have the meanings defined above, or
(c) reacting a compound having the general formula VII

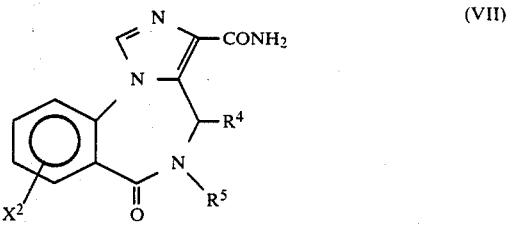

wherein $X^2$, $R^4$ and $R^5$ have the meanings set forth above, with a compound having the general formula VIII

(VIII)

wherein R¹ has the meaning set forth above, to form a compound having the general formula IX

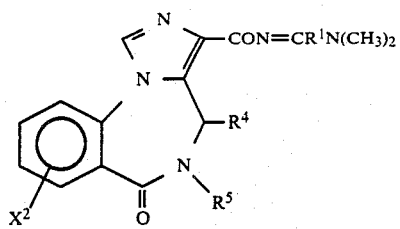 (IX)

wherein X², R⁴, R⁵ and R¹ have the meanings set forth above and reacting the compound having the formula (IX) with NH₂OH or another aminating agent, such as O-(mesitylenesulfonyl)-hydroxylamine, to form a compound having the general formula I, wherein X¹ is

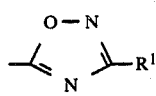

wherein R¹ has the meaning defined above, or
(d) reacting a compound having the general formula X

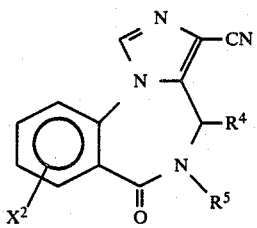 (X)

wherein X², R⁴ and R⁵ have the meanings set forth above, with NH₂OH to form a compound having the general formula XI

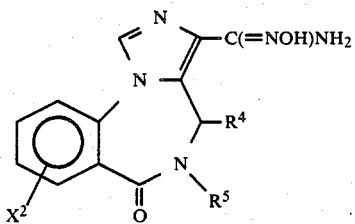 (XI)

wherein X², R⁴ and R⁵ have the meanings set forth above, and reacting the compound having the formula (XI) with R¹—COCl or (R¹CO)₂O, wherein R¹ has the meaning set forth above, to form a compound of formula I, wherein X¹ is

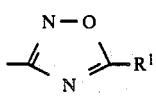

wherein R¹ has the meaning set forth above, or
(e) reacting a reactive derivative, such as an ester derivative, of a compound having the general formula XII

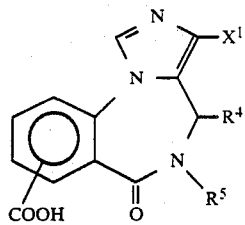 (XII)

wherein R⁴, R⁵ and X¹ have the meanings set forth above, with a compound having the general formula XIII

R¹—C(=NOH)NH₂ (XIII)

wherein R¹ has the meaning set forth above to form a compound of the general formula I wherein X¹, R⁴ and R⁵ have the meanings defined above and wherein X² is

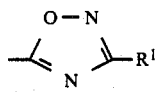

wherein R¹ has the meaning set forth above, optionally via an intermediate compound having the formula XIV

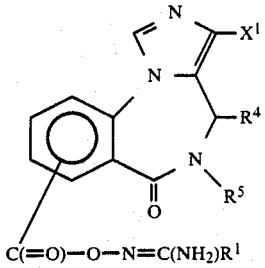 (XIV)

C(=O)—O—N=C(NH₂)R¹ wherein X¹, R¹, R⁴ and R⁵ have the meanings defined above, or
(f) reacting a compound having the general formula XV

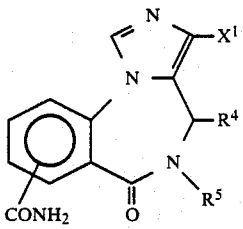 (XV)

wherein X¹, R⁴ and R⁵ have the meanings set forth above, with a compound having the general formula XVI

R¹—C(OCH₃)₂N(CH₃)₂ (XVI)

wherein R¹ has the meaning set forth above, to form a compound having the general formula XVII

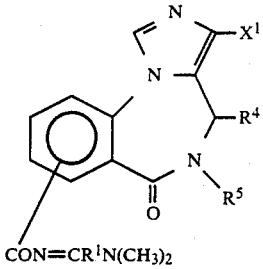

(XVII)

CON=CR¹N(CH₃)₂ wherein X¹, R⁴, R⁵ and R¹ have the meanings set forth above, and reacting the compound having the formula (XVII) with NH₂OH or another aminating agent, such as O-(mesitylenesulfonyl)-hydroxylamine, to form a compound having the general formula I, wherein X² is

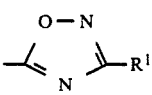

wherein R¹ has the meaning defined above, or
(g) reacting a compound having the general formula XVIII

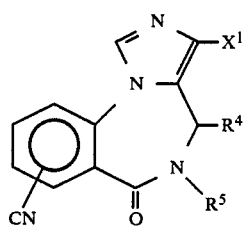

(XVIII)

wherein X¹, R⁴ and R⁵ have the meanings set forth above, with NH₂OH to form a compound having the general formula XVIV

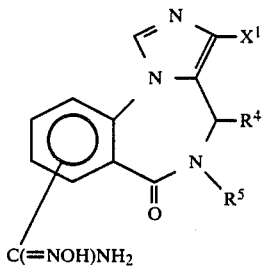

(XVIV)

C(=NOH)NH₂ wherein X¹, R⁴ and R⁵ have the meanings set forth above and reacting the compound having the formula (XVIV) with R¹—COCl or (R¹CO)₂O, wherein R¹ has the meaning set forth above, to form a compound of formula I, wherein X₂ is

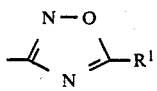

wherein R¹ has the meaning set forth above.

The leaving group, Y, may be any suitable leaving group and, for example, those disclosed in U.S. Pat. Nos. 4,031,079 or 4,359,420, for example, halogen, alkylthio, e.g., methylthio, aralkylthio, N-nitrosoalkylamino, alkoxy, mercapto, —OP(O)(OR)₂ wherein R is lower-alkyl or —OP(O)(NR'R") wherein R' and R" each represents lower-alkyl or phenyl, or together with the nitrogen atom to which they are attached represent a heterocyclic radical such as morpholino, pyrrolidino, piperidino, or methylpiperazino.

The reaction is preferably carried out under alkaline conditions, i.e., in the presence of a base, and among bases alkali metal, e.g., potassium or sodium, alkoxides or hydrides are preferred. The reaction is preferably conducted in the presence of an organic solvent which is nonreactive with the reactants and products of reaction under the conditions of reaction, especially an anhydrous solvent and preferably an anhydrous aprotic solvent such as dimethylformamide (DMF) or the like. The temperature range employed may be any range suitable for the reaction to proceed at a reasonable rate and without undue delay or decomposition and a range from a minus forty (−40) degrees Celsius to about room temperature is accordingly usually particularly suitable.

The starting materials may be prepared from commercially available benzene derivatives and by using well known synthetic methods and as described in Synthesis, Vol. 10, pp. 681–682.

The pharmaceutical properties of the compounds of the invention can be illustrated by determining their capability for displacing radioactivity labelled flunitrazepam from benzodiazepine receptors.

The displacement activity of the compounds of the invention may be found by determining the ED₅₀ value. The ED₅₀ value represents the dose (mg/kg) of a test substance which causes the specific binding of flunitrazepam to benzodiazepine receptors in a living brain to be reduced to 50% of the control value.

Such an in vivo test is carried out as follow:

Principle. Twenty minutes after a dose of ³H-flunitrazepam (³H-FNM) (200 μCi/kg, i.v.) the amount of specific ³H-FNM binding to brain benzodiazepine receptors has reached its maximal value. This specific binding of ³H-FNM can be partly or completely prevented by simultaneous or prior administration of pharmacologically active benzodiazepines and by some benzodiazepine-like agents (Chang and Snyder, Eur. J. Pharmacol. 48, 212–218 (1978)).

Test procedure. Suspensions of test substances (2 mg/ml) are prepared in 5% Duphasol-X (TM Duphar, caster oil-ethylene oxide derivative for emulsifying and solubilizing oil and other water-insoluble substances) by sonification for 10 min using a Branson B15 microtip ultrasonifier (setting 7). Groups of three mice (female, NMR, 18–22 grams) are injected with the test substance at 100 mg/kg intraperitoneally. Fifteen minutes after test substance administration the mice are challenged with 4 μCi intravenously of ³H-FNM (70–90 Ci/mole) in 200 μl physiological saline. Twenty minutes after ³H-FNM administration mice are sacrificed by decapitation, the forebrains rapidly excised (within 30 sec) and homogenized in 12 ml of icecold 25 mM KH₂PO₄, pH 7.1, using an Ultra-Turrax TM homogenizer fitted with an N 10 shaft. Two aliquots of 1 ml are immediately filtered through Whatman GF/C glassfibre filters and washed with 2×5 ml of the above mentioned buffer. The amounts of radioactivity on the filters are determined by conventional scintillation counting. One group of untreated mice serves as control. One to three mice are injected with 25 μg/kg clonazepam i.p. 30 minutes before ³H-FNM to determine the amount of non-specific ³H-FNM binding, which should be between 8-15% of total binding. When doses of 100 mg/kg inhibit more than 50% of specific ³H-flunitrazepam binding, test substances are administered in doses, which are factors of 3.16 times lower than 100 mg/kg. The $ED_{50}$ for a test substance is defined as that dose which inhibits 50% of specific ³H-FNM binding. Specific binding is the amount of binding in controls minus the amount of binding in clonazepam-treated mice.

Results. The $ED_{50}$ value is determined from dose response curves. If only one dose of test substance is administered the $ED_{50}$ value is calculated as follows, provided that the inhibition of specific binding is within the range of 25-75%:

$$ED_{50} = \text{(administration dose)} \times \frac{1}{\left(\frac{C_o}{C_x} - 1\right)} \text{ mg/kg}$$

where $C_o$ is specific binding in controls of $C_x$ is specific binding in mice treated with test substance.

Test results obtained by testing some compounds of the invention will appear from the following Table I.

TABLE 1

[Chemical structure with substituents $X^2$, $R^4$, $R^5$, $X^1$]

| $X^2$ | $R^4$ | $R^5$ | $X^1$ | In vivo displacement activity: $ED_{50}$ (mg/kg) |
|---|---|---|---|---|
| (phenyl with CO₂CH₃) | H | CH₃ | [O—N, N, cyclopropyl] | 0.4 |
| (phenyl with CO₂CH₂CH₃) | H | CH₃ | [O—N, N, cyclopropyl] | 1.4 |
| (phenyl with O—N=) | H | CH₃ | [O—N, N, CH₃] | 1.3 |

TABLE 1-continued

| $X^2$ | $R^4$ | $R^5$ | $X^1$ | In vivo displacement activity: $ED_{50}$ (mg/kg) |
|---|---|---|---|---|
| (phenyl with CH₃, O=N) | H | CH₃ | [N—O, N, CH₃] | 1.7 |
| (phenyl with CO₂CH₂CH₃) | H | CH₃ | [N—O, N, CH₃] | 1.5 |

The compounds of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use; in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) milligram of active ingredient or, more broadly, one (1) to one hundred (100) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, a compound of the invention is dispensed in unit dosage form comprising 1-100 mg in a pharmaceutically-acceptable carrier per unit dosage.

A typical tablet which may be prepared by conventional tabletting techniques contains:

| Active compound | 1.0 mg |
| --- | --- |
| Lactosum | 67.8 mg Ph. Eur. |
| Avicel ® | 31.4 mg |
| Amberlite ® IRP 88 | 1.0 mg |
| Magnesii stearas | 0.25 mg Ph. Eur. |

Due to their high degree of affinity for the benzodiazepine receptors, the compounds of the invention are extremely useful in the treatment of central nervous system ailments or disorders, when administered in an amount effective for the alleviation, amelioration, or elimination thereof. The important CNS activity of the compounds of the invention includes both anticonvulsant and anxiolytic activities along with a low toxicity, together presenting a most favorable therapeutic index. The compounds of the invention may accordingly be administered to a subject, e.g., a living animal body, including a human, in need of the same for the treatment, alleviation, amelioration, or elimination of an indication, associated with the central nervous system and the so-called benzodiazepine receptors, which requires such psychopharmaceutical treatment, e.g., especially convulsion and/or anxiety states, if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their benzodiazepine receptor affinity. Suitable dosage ranges are 1-100 milligrams daily, preferably 1-30 milligrams daily, and especially 1-10 milligrams daily, depending as usual upon the exact mode of administration, form in which administered, the indication toward which the administration is directed, the subject involved and the body weight of the subject involved, and the preference and experience of the physician or veterinarian in charge. Broader ranges for dosages of the compounds according to this invention are 0.1-100 mg/day, preferably 1-30 mg/day, when administered to patients, e.g., humans, as a drug.

The invention will now be described in further detail with reference to the following examples:

EXAMPLE 1

5-Ethoxycarbonyl-1,2-dihydro-4H-3,1-benzoxazine-2,4-dione

A mixture of 6-ethoxycarbonyl-3-amino-benzoic acid hydrochloride (25 g) and phosgene (70 mg, 30% solution in toluene) was refluxed for 2 hours in 300 ml dry dioxane. The solution was then evaporated in vacuo to give the title compound as a crystalline powder. M.p. 188.5°–189.6° C.

EXAMPLE 2

6-ethoxycarbonyl-3,4-dihydro-4-methyl-3H-1,4-benzodiazepine-2,5-(1H)-dione

A mixture of 5-ethoxycarbonyl-1,2-dihydro-4H-3,1-benzoxazine-2,4-dione (23.5 g) and sarcosine (9.5 g) in 200 ml dimethyl sulfoxide (DMSO) was heated to 130° C. with stirring. After four hours the solution was cooled to room temperature and the solvent was removed in vacuo. The residue was treated with ethylacetate, whereupon the title compound precipitated as pale yellow crystals. The crystals were collected by filtration. M.p. 187.7°–188.5° C.

EXAMPLE 3

(S)-6-ethoxycarbonyl-1,2,3,11a-tetrahydro-5H-pyrrolo(2,1-c)-(1,4)benzodiazepine-5,11(1H)-dione A mixture of 5-ethoxycarbonyl-1,2-dihydro-4H-3,1-benzoxazine-2,4-dione (5.5 g) and L-proline was heated with stirring to 140° C. in 75 ml DMSO. After 4½ hours the solution was cooled to room temperature and evaporated in vacuo. The residue was partitioned between methylene chloride/water and the organic phase was separated, dried over $MgSO_4$ and evaporated to give the title compound as light brown crystals. M.p. 188°–188.2° C.

EXAMPLE 4

3-cyclopropyl-5-isocyanomethyl-1,2,4-oxadiazole a.

3-cyclopropyl-5-formylaminomethyl-1,2,4-oxadiazole

A solution of ethyl formylaminomethyl-carboxylate (150 mmol) and cyclopropyl carboxamide oxime (100 mmol) in 100% EtOH (100 ml) was charged with Na (200 mg) and crushed molecular sieves (4 Å) (10 g). The mixture thus obtained was stirred and heated to reflux for 8 hours. The mixture was cooled to room temperature, filtered through filter aid and the filtrate was evaporated in vacuo. The oily residue was partitionated into a $CHCl_3$ phase which was dried with $Na_2SO_4$ and evaporated.

b. 3-cyclopropyl-5-isocyanomethyl-1,2,4-oxadiazole

A stirred solution of 3-cyclopropyl-5-formylaminomethyl-1,2,4-oxadiazole (60 mmol) and triethylamine (176 mmol) in $CH_2Cl_2$ (100 ml) was charged dropwise with $POCl_3$ (60 mmol) at 0° C. The mixture was then left for 30 minutes with stirring at 0° C., whereafter a solution of $Na_2CO_3$ (60 mmol) in $H_2O$ (50 ml) was added. The mixture was heated to room temperature, whereafter the organic phase was separated, dried and evaporated in vacuo. The residue was treated with ether, decanted and the solution was evaporated to give the title compound as an oil. The oil was processed without any further purification. The compound was characterized by its IR absorbtion band at 2160 $cm^{-1}$. 3-ethyl-5-isocyanomethyl-1,2,4-oxadiazole was prepared from 3-ethyl-5-formylaminomethyl-1,2,4-oxadiazole in a similar manner. IR: $cm^{-1}$: 2170.

EXAMPLE 5

5-cyclopropyl-3-isocyanomethyl-1,2,4-oxadiazole a. Formylaminomethyl-carboxamide oxime 0.55 mmol of freshly liberated hydroxylamine dissolved in 370 ml methanol was added to 53.6 g (0.638 mmol) N-formylamino-acetonitrile. An ice bath was used to keep the temperature below 20° C. during addition. The solution was allowed to stand at room temperature overnight, whereafter it was evaporated to give the title compound as pale crystals. Decomp. 104°–110° C.

b. 3-formylaminomethyl-5-cyclopropyl-1,2,4-oxadiazole

A mixture of 35 ml ethyl cyclopropylcarboxylate, 20 g formylamino-methylcarboxamide oxime, 1 g sodium and 30 g of crushed molecular sieves (4 Å) was refluxed in 300 ml abs. EtOH for 8 hours whereafter a further 1 g sodium was added. The reaction mixture was filtered and the filtrate was evaporated. The dark oily residue was suspended in 300 ml $CHCl_3$, filtered, and the filtrate was evaporated to give the title compound as an oil. H-NMR (60 MHz, $CDCl_3$) (ppm): 1.2 (4H, m), 2.8 (1H, m), 4.5 (2H, d, J=6 Hz), 7.8 (1H, broad-NH), 8.2 (1H, s).

The following compounds were synthesized from the appropriate ethyl esters in a similar manner:
3-Formylaminomethyl-5-ethyl-1,2,4-oxadiazole. H-NMR (60 MHz, $CDCl_3$) (ppm): 1.4 (3H, t, J=8 Hz), 2.9 (2H, q, J=8 Hz) 4.55 (2H, s), 7.8 (1H, broad-NH), 8.25 (1H, s). 3-Formylaminomethyl-5-methyl-1,2,4-oxadiazole. H-NMR (60 MHz, $CDCl_3$) (ppm); 2.6 (3H, s), 4.6 (2H, d, J=3 Hz), 7.4 (1H, broad-NH), 8.25 (1H, s).
3-Formylaminomethyl-5-methoxymethyl-1,2,4-oxadiazole H-NMR (60 MHz, $CDCl_3$) (ppm): 3.5 (3H, s), 4.7 (4H, s+d, J=6 Hz), 7.8 (1H, broad-NH), 8.25 (H, s).

c. 5-Cyclopropyl-3-isocyanomethyl-1,2,4-oxadiazole

A stirred solution of 5-cyclopropyl-3-formylamino-methyl-1,2,4-oxadazole (60 mmol) and triethylamine (176 mmol) in $CH_2Cl_2$ (100 ml) was charged dropwise with $POCl_3$ (60 mmol) at 0° C. The mixture was then left for 30 minutes with stirring at 0° C., whereafter a solution of $Na_2CO_3$ (60 mmol) in $H_2O$ (50 ml) was added. The mixture was heated to room temperature, whereafter the organic phase was separated, dried and evaporated in vacuo. The residue was treated with ether, decanted and the solution was evaporated to give the title compound as an oil. The oil was processed without any further purification. The compound was characterized by its IR absorbtion band at 2160 $cm^{-1}$.

5-Ethyl-3-isocyanomethyl-1,2,4-oxadiazole, 5-methyl-3-isocyanomethyl-1,2,4-oxadiazole, and 5-methoxymethyl-3-isocyanomethyl-1,2,4-oxadiazole were prepared in a similar manner. All compounds were oils and were characterized by their IR stretching band at 2160 $cm^{-1}$.

EXAMPLE 6

Methoxyacetamide oxime 2.3 g of sodium in 33 ml of dry methanol was mixed with 6.55 g of hydroxylamine hydrochloride in 66 ml of dry methanol. The mixture was filtered and 7.8 g of methoxyacetonitrile was added dropwise to the filtrate. The mixture was left for 48 hours. The mixture was then cooled to 4° C. Filtration and evaporation of the filtrate give 8.7 g of the title compound.

The following compounds were synthesized from the appropriate nitriles in an analogous manner:
Propionamide oxime
Cyclopropyl carboxamide oxime
Isopropyl carboxamide oxime
Acetamide oxime
Phenylcarboxamide oxime

EXAMPLE 7

Diethyl 5,6-dihydro-5-methyl-6-oxo-4H-imidazo(1,5-a)(1,4)benzodiazepine-3,7-dicarboxylate 6-Ethoxycarbonyl-3,4-dihydro-4-methyl-2H-1,4-benzodiazepine-2,5(1H)-dione (10 mmol) was dissolved in 25 ml dry dimethylformamide (DMF). While stirring, K-t-butoxide (12 mmol) was added and the mixture was thereafter cooled to −20° C. A −30° C. cold solution of K-t-butoxide (12 mmol) in dry DMF (15 ml) was charged with isocyano-acetic acid ethylester (12 mmol). This solution was added to the above mentioned solution, and the combined solution was stirred at room temperature for 2 hours. 2 ml of acetic was added, whereafter the solution was evaporated to dryness. The oily residue was subjected to $SiO_2$-purification with acetone/chloroform ($\frac{1}{3}$) as eluent. This yielded the title compound as a crystalline powder. M.p. 136.3°–139.9° C.

The following were synthesized in a similar manner from the appropriate benzodiazepine diones and isonitriles:
(S)-1-(3-cyclopropyl-1,2,4-oxadiazol-5-yl)-8-ethoxycarbonyl-11,12,13,13a-tetrahydro-9-oxo-9H-imidazo(1,5-a)pyrrolo(2,1-c)(1,4)benzodiazepine by reacting
(S)-6-ethoxycarbonyl-1,2,3,11a-tetrahydro-5H-pyrrolo(2,1-c)(1,4)benzodiazepine-5,11(10H)-dione with 3-cyclopropyl-5-isocyanomethyl-1,2,4-oxadiazole. M.p. 97.2°–97.4° C.
7-Ethoxycarbonyl-5,6-dihydro-5-methyl-3-(5-methoxymethyl-1,2,4-oxadiazol-3-yl)-6-oxo-4H-imidazo(1,5-a)(1,4)benzodiazepine by reacting
6-ethoxycarbonyl-3,4-dihydro-4-methyl-2H-1,4-benzodiazepine-2,5(1H)-dione with
3-isocyanomethyl-5-methoxymethyl-1,2,4-oxadiazole. M.p. 116.0°–116.9° C.

3-(3-Cyclopropyl-1,2,4-oxadiazol-5-yl)-7-ethoxycarbonyl-5,6-dihydro-5-methyl-6-oxo-4H-imidazo(1,5-a)(1,4)benzodiazepine by reacting
6-ethoxycarbonyl-3,4-dihydro-4-methyl-2H-(1,4)-benzodiazepine-2,5(1H)-dione with
3-cyclopropyl-5-isocyanomethyl-1,2,4-oxadiazole.
M.p. 169.9°–170.2° C.
3-(3-Cyclopropyl-1,2,4-oxadiazol-5-yl)-5,6-dihydro-7-methoxycarbonyl-5-methyl-6-oxo-4H-imidazo(1,5-a)(1,4)benzodiazepine by reacting
3,4-dihydro-6-methoxycarbonyl-4-methyl-2H-(1,4)-benzodiazepine-2,5(1H)-dione with
3-cyclopropyl-5-isocyanomethyl-1,2,4-oxadiazole.
M.p. 199.4°–199.5° C.
7-Ethoxycarbonyl-5,6-dihydro-5-methyl-3-(5-methyl-1,2,4-oxadiazol-3-yl)-6-oxo-4H-imidazo(1,5-a)(1,4)benzodiazepine by reacting
6-ethoxycarbonyl-3,4-dihydro-4-methyl-2H-(1,4)-benzodiazepine-2,5(1H)-dione with
3-isocyanomethyl-5-methyl-1,2,4-oxadiazole.
M.p. 205.7°–205.9° C.
3-(5-Cyclopropyl-1,2,4-oxadiazol-3-yl)-5,6-dihydro-7-methoxycarbonyl-5-methyl-6-oxo-4H-imidazo(1,5-a)(1,4)benzodiazepine by reacting
3,4-dihydro-6-methoxycarbonyl-4-methyl-2H-1,4-benzodiazepine-2,5(1H)-dione with
5-cyclopropyl-3-isocyanomethyl-1,2,4-oxadiazole.
M.p. 230.7°–232°8 C.
3-(5-cyclopropyl-1,2,4-oxadiazol-3-yl)-5,6-dihydro-7-ethoxycarbonyl-5-methyl-6-oxo-4H-imidazo(1,5-a)(1,4)benzodiazepine by reacting
3,4-dihydro-6-ethoxycarbonyl-4-methyl-2H-1,4-benzodiazepine-2,5(1H)-dione with
3-isocyanomethyl-5-cyclopropyl-1,2,4-oxadiazole.
M.p. 178.2°–179.2° C.

EXAMPLE 8

3,7-Bis-(3-ethyl-1,2,4-oxadiazol-5-yl)-5,6-dihydro-5-methyl-6-oxo-4H-imidazo(1,5-a)(1,4)benzodiazepine A mixture of diethyl-5,6-dihydro-5-methyl-6-oxo-4H-imidazo(1,5-a)(1,4)benzodiazepine-3,7-dicarboxylate (500 mg), propionamideoxime (500 mg), sodium ethanolate (120 mg) and 5 g crushed molecular sieves (4 Å) was refluxed for 3 hours in 40 ml dry ethanol. The mixture was cooled to room temperature and the crushed molecular sieves filtered off, whereafter the filtrate was evaporated to give the product as an oily residue which was crystallized in water.
M.p. 172.8°–174.3° C.

The following compounds were made in a similar manner:
5,6-Dihydro-3-(5-methyl-1,2,4-oxadiazol-3-yl)-5-methyl-6-oxo-7-(3-phenyl-1,2,4-oxadiazol-5-yl)-4H-imidazo(1,5-a)(1,4)benzodiazepine by reacting
7-ethoxycarbonyl-5,6-dihydro-5-methyl-3-(5-methyl-1,2,4,-oxadiazol-3-yl)-6-oxo-4-imidazo(1,5-a)(1,4)benzodiazepine with
phenylcarboxamidoxime.
M.p. 244.6°–246.2° C.
7-(3-Cyclopropyl-1,2,4-oxadiazol-5-yl)-5,6-dihydro-5-methyl-3-(5-methyl-1,2,4-oxadiazol-3-yl)-6-oxo-4H-imidazo(1,5-a)(1,4)benzodiazepine by reacting
7-ethoxycarbonyl-5,6-dihydro-5-methyl-3-(5-methyl-1,2,4-oxadiazol-3-yl)-6-oxo-4H-imidazo(1,5-a)(1,4)benzodiazepine with
cyclopropyl carboxamide oxime.
M.p. 249.6°–250.8° C.

3-(5-cyclopropyl-1,2,4-oxadiazol-3-yl)-7-(3-methyl-1,2,4-oxadiazol-5-yl)-5,6-dihydro-5-methyl-6-oxo-4H-imidazo(1,5-a)(1,4)benzodiazepine by reacting
3-(5-cyclopropyl-1,2,4-oxadiazol-3-yl)-7-ethoxycarbonyl-5,6-dihydro-5-methyl-6-oxo-4H-imidazo(1,5-a)(1,4)benzodiazepine with
acetamide oxime.
M.p. 246.4°–246.5° C.

EXAMPLE 9

5,6-Dihydro-7-(2-hydroxyethoxycarbonyl)-5-methyl-3-(5-methyl-1,2,4-oxadiazol-3-yl)-6-oxo-4H-imidazo(1,5-a)(1,4)benzodiazepine 7-Ethoxycarbonyl-5,6-dihydro-5-methyl-3-(5-methyl-1,2,4-oxadiazol-3-yl)-6-oxo-4H-imidazo(1,5-a)(1,4)benzodiazepine (500 mg) was dissolved in ethylene glycol (20 ml) and 3 drops of concentrated sulphuric acid were added. The solution was then stirred at 130° C. for 24 hours, cooled and partitioned between water (150 ml) and CHCl₃ (150 ml). The organic phase was separated, dried over Na₂SO₄, and evaporated to give the title compound as white crystals.
M.p. 224.4°–226° C.

In conclusion, from the foregoing, it is apparent that the present invention provides novel neurologically-effective benzodiazepine receptor binding imidazobenzodiazepine compounds and salts thereof, having advantageous and unpredictable properties, as well as novel pharmaceutical compositions thereof and method of treating therewith, all possessed of the foregoing more specifically-enumerated characteristics and advantages.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope of the appended claims.

I claim:

1. Benzodiazepine derivatives having the formula I

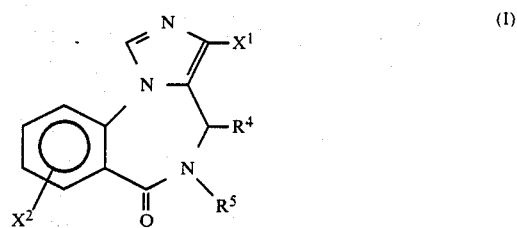

wherein
X¹ and X² independently are

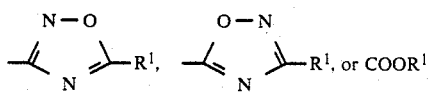

wherein R¹ is $C_{1-3}$-alkyl, $C_{3-5}$-cycloalkyl, $C_{1-3}$-alkoxymethyl, $C_{1-3}$-hydroxyalkyl, or aryl,
R⁴ is hydrogen, and
R⁵ is $C_{1-6}$-alkyl, or wherein R⁴ and R⁵ together form a 2–4 membered alkylene chain.

2. A compound of claim 1 which is 7-Ethoxycarbonyl-5,6-dihydro-5-methyl-3-(3-cyclopropyl-1,2,4- oxadiazol-5-yl)-6-oxo-4H-imidazo(1,5-a)(1,4)benzodiazepine.

3. A compound of claim 1 which is 7-Ethoxycarbonyl-5,6-dihydro-5-methyl-3-(5-methyl-1,2,4-oxadiazol-3-yl)-6-oxo-4H-imidazo(1,5-a)(1,4)benzodiazepine.

4. A compound of claim 1 which is 7-(3-phenyl-1,2,4-oxadiazol-5-yl)-5,6-dihydro-5-methyl-3-(5-methyl-1,2,4-oxadiazol-3-yl)-6-oxo-4H-imidazo(1,5-a)(1,4)benzodiazepine.

5. A pharmaceutical composition suitable for use in the treatment of a central nervous system ailment comprising an amount of a compound of claim 1 which is effective for the alleviation of such disorder together with a pharmaceutically-acceptable carrier or diluent.

6. A pharmaceutical composition according to claim 5 in the form of an oral dosage unit containing 1-100 mg of the active compound.

7. A method of treating a central nervous system ailment in a subject in need of such treatment comprising the step of administering to said subject an amount of a compound of claim 1 which is effective for the alleviation of such ailment.

8. A method according to claim 7 of treating a central nervous system ailment in a subject in need of such treatment comprising the step of administering to said subject an amount of a compound of claim 1 which is effective for the alleviation of such ailment in the form af a pharmaceutical composition thereof, in which it is present together with a pharmaceutically-acceptable carrier or diluent.

9. A method of preparing a compound according to claim 1, having the formula I

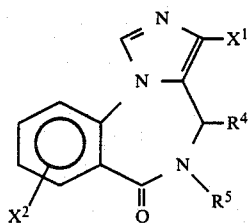
(I)

wherein
$X^1$ and $X^2$ independently are

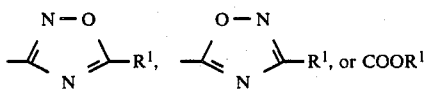

wherein $R^1$ is $C_{1-3}$-alkyl, $C_{3-5}$-cycloalkyl, $C_{1-3}$-alkoxymethyl, $C_{1-3}$-hydroxyalkyl, or aryl,
$R^4$ is hydrogen, and
$R^5$ is $C_{1-6}$-alkyl, or wherein $R^4$ and $R^5$ together form a 2-4 membered alkylene chain,
Characterized in
reacting a reactive derivative, such as an ester derivative, of a compound having the general formula XII

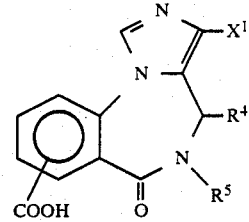
(XII)

wherein $R^4$, $R^5$ and $X^1$ have the meanings set forth above, with a compound having the general formula XIII $R^1$—C(=NOH)NH$_2$ (XIII)

wherein $R^1$ has the meaning set forth above to form a compound of the general formula I wherein $X^1$, $R^4$ and $R^5$ have the meanings defined above and wherein $X^2$ is

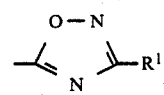

wherein $R^1$ has the meaning set forth above, optionally via an intermediate compound having the formula XIV

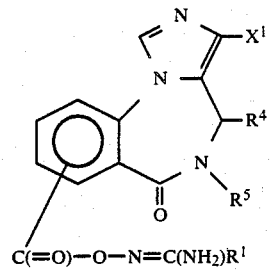
(XIV)

C(=O)—O—N=C(NH$_2$)R$^1$ wherein $X^1$, $R^1$, $R^4$ and $R^5$ have the meanings defined above.

10. A method of preparing a compound according to claim 1, having the formula I

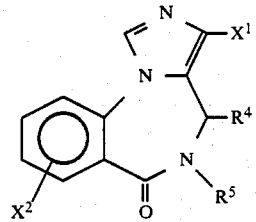
(I)

wherein
$X^1$ and $X^2$ independently are

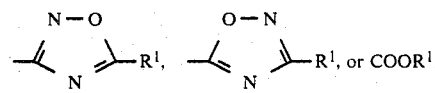

wherein $R^1$ is $C_{1-3}$-alkyl, $C_{3-5}$-cycloalkyl, $C_{1-3}$-alkoxymethyl, $C_{1-3}$-hydroxyalkyl, or aryl, R⁴ is hydrogen, and R⁵ is $C_{1-6}$-alkyl, or wherein R⁴ and R⁵ together form a 2-4 membered alkylene chain, Characterized in reacting a compound having the general formula XV

[Structure XV: benzene ring with imidazole substituent bearing X¹, CHR⁴-N(R⁵)-C(=O)-, and CONH₂ groups] (XV)

wherein X¹, R⁴ and R⁵ have the meanings set forth above, with a compound having the general formula XVI $$R^1-C(OCH_3)_2N(CH_3)_2 \quad (XVI)$$

wherein R¹ has the meaning set forth above, to form a compound having the general formula XVII

[Structure XVII: similar to XV but with CON=CR¹N(CH₃)₂ group] (XVII)

CON=CR¹N(CH₃)₂ wherein X¹, R⁴, R⁵ and R¹ have the meanings set forth above and reacting the compound having the formula (XVII) with NH₂OH or another aminating agent, such as O-(mesitylenesulfonyl)-hydroxylamine, to form a compound having the general formula I, wherein X² is

[Structure: oxadiazole ring O—N, —R¹]

wherein R¹ has the meaning defined above.

11. A method of preparing a compound according to claim 1, having the formula I

[Structure I: benzene ring with imidazole bearing X¹, CHR⁴-N(R⁵)-C(=O)-, and X² substituents] (I)

wherein

X¹ and X² independently are

[Structures: N—O/N oxadiazole —R¹, O—N/N oxadiazole —R¹, or COOR¹]

wherein R¹ is $C_{1-3}$-alkyl, $C_{3-5}$-cycloalkyl, $C_{1-3}$-alkoxymethyl, $C_{1-3}$-hydroxyalkyl, or aryl, R⁴ is hydrogen, and R⁵ is $C_{1-6}$-alkyl, or wherein R⁴ and R⁵ together form a 2-4 membered alkylene chain, Characterized in reacting a compound having the general formula XVIII

[Structure XVIII: benzene with imidazole-X¹, CHR⁴-N(R⁵)-C(=O)-, and CN groups] (XVIII)

wherein X¹, R⁴ and R⁵ have the meanings set forth above, with NH₂OH to form a compound having the general formula XVIV

[Structure XVIV: similar with C(=NOH)NH₂ group] (XVIV)

C(=NOH)NH₂ wherein X¹, R⁴ and R⁵ have the meanings set forth above and reacting the compound having the formula (XVIV) with R¹—COCl or (R¹CO)₂O, wherein R¹ has the meaning set forth above, to form a compound of formula I, wherein X² is

[Structure: N—O/N oxadiazole —R¹]

wherein R¹ has the meaning set forth above.

* * * * *

UNITED STATES PATENT AND TRADEMARK OFFICE
CERTIFICATE OF CORRECTION

PATENT NO. : 4,772,599
DATED : September 20, 1988
INVENTOR(S) : Frank Wätjen

It is certified that error appears in the above-identified patent and that said Letters Patent is hereby corrected as shown below:

Col. 6, line 38; "follow:" should read -- follows: --
Col. 6, line 50; "caster" should read -- castor --
Col. 7, line 21; "administration" should read -- administered --
Col. 11, line 50; after the period, start a new paragraph with "3-Formylaminomethyl-"
Col. 13, line 57; "-oxo-4-" should read -- -oxo-4H- --
Col. 14, line 42; delete "1. Benzodiazepine derivatives having the" and insert -- 1. A compound of the --
Col. 15, line 33; "af" should read -- of --

Signed and Sealed this

Eighth Day of August, 1989

Attest:

DONALD J. QUIGG

Attesting Officer

Commissioner of Patents and Trademarks